United States Patent
Mo et al.

(10) Patent No.: US 8,530,839 B2
(45) Date of Patent: Sep. 10, 2013

(54) APPARATUS AND METHOD FOR MEASURING PUNGENCY OF RED PEPPER POWDER

(75) Inventors: Chang Yeun Mo, Bucheon-si (KR); Kang Jin Lee, Hwaseong-si (KR); Jae Ryong Son, Suwon-si (KR); Hyun Dong Lee, Suwon-si (KR); Jai Gyu Kim, Suwon-si (KR); Sukwon Kang, Seoul (KR); Gil Mo Yang, Suwon-si (KR)

(73) Assignee: Rural Development Administration, Gyeonggi-Do (KR)

( * ) Notice: Subject to any disclaimer, the term of this patent is extended or adjusted under 35 U.S.C. 154(b) by 587 days.

(21) Appl. No.: 12/828,972

(22) Filed: Jul. 1, 2010

(65) Prior Publication Data

US 2011/0218739 A1 Sep. 8, 2011

(30) Foreign Application Priority Data

Mar. 3, 2010 (KR) ........................ 10-2010-0019178

(51) Int. Cl.
*G01N 31/00* (2006.01)
*G01J 5/00* (2006.01)

(52) U.S. Cl.
USPC ........................................ 250/338.1; 702/23

(58) Field of Classification Search
USPC ..................................................... 250/338.1
See application file for complete search history.

(56) References Cited

U.S. PATENT DOCUMENTS

| | | | | | |
|---|---|---|---|---|---|
| 4,963,743 | A | * | 10/1990 | Satake et al. | 250/339.07 |
| 5,537,202 | A | * | 7/1996 | Komatsu et al. | 356/36 |

FOREIGN PATENT DOCUMENTS

KR   871681 B1 * 12/2008

* cited by examiner

*Primary Examiner* — David Porta
*Assistant Examiner* — Kenneth J Malkowski
(74) *Attorney, Agent, or Firm* — Osha Liang LLP

(57) ABSTRACT

An apparatus for measuring pungency of red pepper powder includes a near infrared measuring unit; a reference spectrum measuring unit; a red pepper powder injecting unit; a red pepper powder height equalizing unit; a red pepper powder transferring unit; a red pepper powder ejecting unit; a display unit; a button unit; and a measurement controller for, if a reference spectrum measurement opening signal is detected, operating a reference spectrum measurement opening and closing unit, injecting the reference material, measuring the spectrum of the reference material, if the reference spectrum measurement closing signal is detected, operating the opening and closing unit, removing the reference material, closing the opening and closing unit, injecting the red pepper powder, and measuring the near infrared spectrum of red pepper powder, correcting near infrared spectrum data to the spectrum of the reference material, calculating a degree of pungency, and displaying the degree of pungency.

15 Claims, 10 Drawing Sheets

APPARATUS AND METHOD FOR MEASURING PUNGENCY OF RED PEPPER POWDER

CROSS-REFERENCE TO RELATED PATENT APPLICATION

This application claims the benefit of Korean Patent Application No. 10-2010-0019178, filed on Mar. 3, 2010, in the Korean Intellectual Property Office, the disclosure of which is incorporated herein in its entirety by reference.

BACKGROUND OF THE INVENTION

1. Field of the Invention

The present invention relates to an apparatus and method for measuring pungency of red pepper powder, and more particularly, to an apparatus and method for quickly measuring pungency of red pepper powder using a near infrared sensor.

2. Description of the Related Art

In general, pungency and red color of peppers are important when peppers are used as food. The pungency of peppers is capsaicinoids compound including mainly capsaicin and dihydrocapsaicin. Capsaicinoids is mainly contained in a placenta between a pepper pericarp and seed and a septum, and partly in the seed closer to the placenta. A fruit flesh ununiformly contains small amount of capsaicinoids.

In accordance with the Korean Standard (KS), red pepper powder is uniform in unique color and gloss, has moisture below 11.0%, ash below 8.0%, acid-insoluble ash below 8.0%. If capsaicinoids of red pepper powder exceeds 42.3 mg %, pepper power is defined as having pungency. If capsaicinoids of red pepper powder is below 42.3 mg %, pepper power is defined as having mild taste.

Meanwhile, Karl Norris analyzed a chemical solid specimen of agricultural products by applying a multivariable analysis method to a complicated near infrared spectrum in the early 1960's, which has been put to practical use of a near infrared spectral analysis method for the first time. Thereafter, the near infrared spectral analysis method has started in an agricultural field and applied to a medical field and food, feed, fiber, petrochemical, and polymer fields as well. The near infrared spectral analysis method enables to minimize pre-processing on specimens and quickly analyze specimens. Further, the near infrared spectral analysis method is a non-destructive method capable of simultaneously measuring a variety of components and repeatedly measuring them in real time.

SUMMARY OF THE INVENTION

Red pepper powder is used for many kinds of food preferred by Koreans. As Koreans become have a variety of dietary life, they have various preferences for pungency of red pepper powder. Therefore, if it is possible to objectively measure the degree of pungency of red pepper powder, Koreans can select their respective desired red pepper powder of pungency, thereby leading to a reasonable dietary life.

The present invention provides an apparatus and method for measuring pungency of red pepper powder by quickly measuring, displaying, and standardizing the degree of pungency of red pepper powder.

According to an aspect of the present invention, there is provided an apparatus for measuring pungency of red pepper powder including: a near infrared measuring unit for measuring a spectrum of a reference material or a near infrared spectrum of red pepper powder that is an object of measurement according to a control signal using a near infrared sensor; a reference spectrum measuring unit for enabling the near infrared measuring unit to measure the spectrum of the reference material; a red pepper powder injecting unit for injecting a sample of the red pepper powder that is the object of measurement; a red pepper powder height equalizing unit for equalizing heights of the red pepper powder injected through the red pepper powder injecting unit in order to increase the accuracy of measurement; a red pepper powder transferring unit for transferring the red pepper powder that is the object of measurement via a transfer belt; a red pepper powder ejecting unit for ejecting the completely measured sample of the red pepper powder; a display unit for displaying an operation state or a degree of pungency of measurement result; a button unit; and a measurement controller for, if a reference spectrum measurement opening signal is detected, operating a reference spectrum measurement opening and closing unit, injecting the reference material, measuring the spectrum of the reference material using the near infrared measuring unit, if the reference spectrum measurement closing signal is detected, operating the reference spectrum measurement opening and closing unit, removing the reference material, closing the reference spectrum measurement opening and closing unit, injecting the red pepper powder, and measuring the near infrared spectrum of red pepper powder using the near infrared measuring unit, correcting near infrared spectrum data of the red pepper powder input from the near infrared measuring unit to the spectrum of the reference material, calculating a degree of pungency according to a capsaicinoids content measurement recurrence model, and displaying the degree of pungency on the display unit.

According to another aspect of the present invention, there is provided a method of measuring pungency of red pepper powder including: measuring a spectrum of a reference material if the reference material or a reference spectrum measurement hole of a transfer belt is at a position for measuring a near infrared sensor; injecting red pepper powder that is an object of measurement to the transfer belt; equalizing heights of the red pepper powder injected to the transfer belt; measuring a near infrared spectrum of the red pepper powder using the near infrared measuring unit; correcting the near infrared spectrum of the red pepper powder to the spectrum of the reference material; calculating a degree of pungency of the red pepper powder with a capsaicinoids content measurement recurrence modeling method using the corrected near infrared spectrum data of the red pepper powder; and displaying the calculated degree of pungency.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. This invention may, however, be embodied in many different forms and should not be construed as being limited to the embodiments set forth herein.

An apparatus for measuring pungency of red pepper powder of the present invention includes a first embodiment in which a reference spectrum measuring unit is positioned in an upper portion of a transfer belt, and a second embodiment in which the reference spectrum measuring unit is positioned in a lower portion of the transfer belt.

First Embodiment

Figure 1:
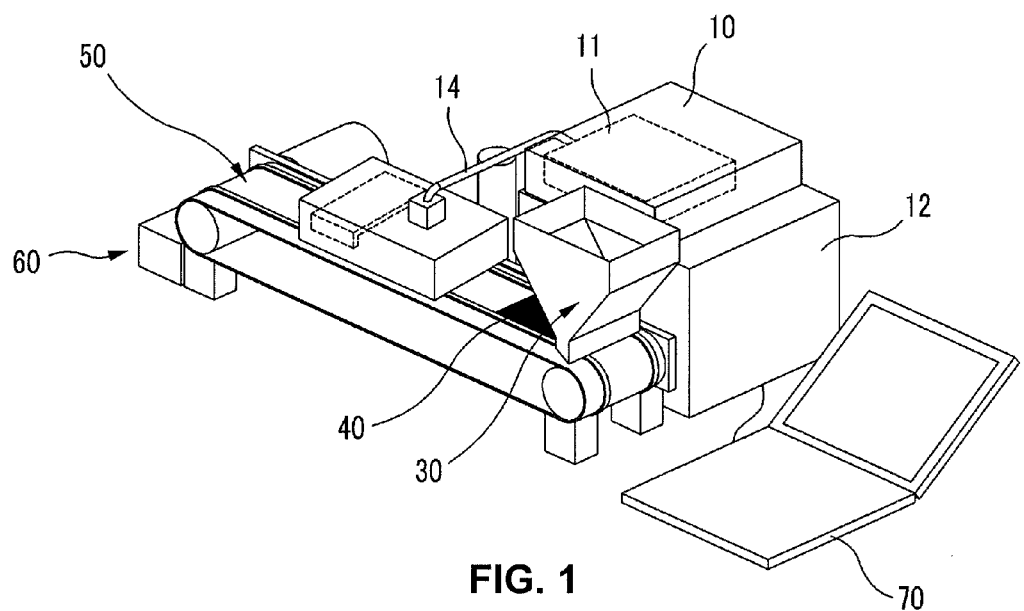
FIG. 1 is a perspective view of an apparatus for measuring pungency of red pepper powder according to a first embodiment of the present invention.
Figure 2:
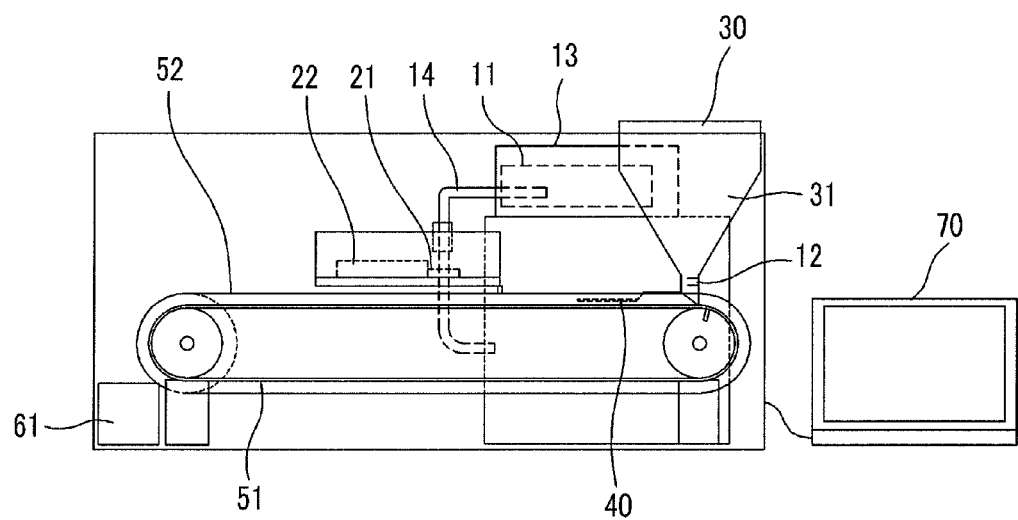
FIG. 2 is a plan view of the apparatus for measuring pungency of red pepper powder according to the first embodiment of the present invention.

FIG. 1 is a perspective view of an apparatus for measuring pungency of red pepper powder according to a first embodiment of the present invention. FIG. 2 is a plan view of the apparatus for measuring pungency of red pepper powder according to the first embodiment of the present invention.

Referring to FIGS. 1 and 2, a mechanical composition of the apparatus for measuring pungency of red pepper powder according to the present invention includes a near infrared measuring unit 10 for measuring a spectrum of a reference material 21 and measuring a spectrum of red pepper powder that is an object of measurement using a near infrared sensor 11 including a light emitting unit and a light receiving unit, a reference spectrum measuring unit 20 for enabling the near infrared measuring unit 10 to measure the spectrum of the reference material 21, a red pepper powder injecting unit 30 for injecting a sample of the red pepper powder that is the object of measurement, a red pepper powder height equalizing unit 40 for equalizing heights of the red pepper powder in order to increase the accuracy of measurement, a red pepper powder transferring unit 50 for transferring the red pepper powder that is the object of measurement via a transfer belt 51, a red pepper powder ejecting unit 60 for ejecting the completely measured sample of the red pepper powder, and a PC 70 connected to the near infrared measuring unit 10 and for computing pungency according to the measured spectrum. The PC 70, which is a notebook in which a program for controlling the apparatus and measuring pungency of the red pepper powder is installed, controls a driving signal of the apparatus for measuring pungency of the red pepper powder and measures pungency of the red pepper powder using the program for measuring pungency. However, as will be described later, the PC 70 may be realized as a measurement controller and integrally embedded in the apparatus for measuring pungency of the red pepper powder.

The near infrared measuring unit 10 includes a light source unit 12, the near infrared sensor 11, a near infrared sensing probe 14, and a near infrared sensor constant temperature device 13. The light source unit 12 includes the light emitting unit and a light irradiating unit, connects one side of the near infrared sensing probe 14 to the light irradiating unit, and irradiates light to the red pepper powder or a measurement material through the near infrared sensing probe 14. The near infrared sensor 11 is included in one side near the light source unit 12, is connected to one side of the near infrared sensing probe 14 and the PC 70, measures a reflective absorbance of the red pepper powder or a measurement sample through the near infrared sensing probe 14, and transmits a measured spectrum to the PC 70. The near infrared sensor constant temperature device 13 includes the near infrared sensor 11, and maintains a constant temperature of the near infrared sensor 11. If the temperature of the near infrared sensor 11 changes, the measured absorbance changes, which increases a measurement error, and thus the near infrared sensor constant temperature device 13 removes the measurement error.

The reference spectrum measuring unit 20 for automatically correcting a near infrared absorbance according to the first embodiment of the present invention is disposed between an upper portion of the transfer belt 51 and the near infrared sensing probe 14, and enables the near infrared measuring unit 10 to measure the spectrum of the reference material 21 by receiving a reference spectrum measurement signal, operating a reference spectrum measurement opening and closing unit 22, and having the reference material 21 positioned in a perpendicular direction to a lower end of the near infrared sensing probe 14.

The near infrared measuring unit 10 is positioned on an upper side of the reference spectrum measuring unit 20 on which near infrared sensor 11 including the light emitting unit and the light receiving unit is positioned. The reference spectrum measuring unit 20 is disposed between the near infrared sensing probe 14 and the red pepper powder. The red pepper powder is positioned on the transfer belt 51 of a lower end of the reference spectrum measuring unit 20. In general, an edible portion of the red pepper powder includes a pericarp, placenta, and seed. Although the placenta is a very small amount, capsaicinoids content of the placenta is several tens of times compared to that of the pericarp or the seed. Thus, although pungency of the red pepper powder is almost determined according to an amount of placenta contained in the red pepper powder, the placenta has an ununiform distribution and thus pungency differs according to sampling. In order to remove such an error of pungency by sampling, the present invention scans surface of the red pepper powder, obtains a near infrared spectrum, and measures spectrum of the whole red pepper powder. Further, the apparatus for measuring pungency of the red pepper powder according to the present invention measures a spectrum of the reference material 21, measures the spectrum of the red pepper powder, and corrects sensitivity of the red pepper powder to the spectrum of the reference material 21 in order to reduce an error of the spectrum of the red pepper powder.

The reference spectrum measuring unit 20 includes the reference material 21, the reference spectrum measurement opening and closing unit 22, and a reference material mounting unit 24. The reference material mounting unit 24 is positioned in a perpendicular lower side of the near infrared measuring unit 10, and has the surface of the reference material 21 mounted in perpendicular to the near infrared measuring unit 10. The reference material 21 is formed of Teflon and is fixed to the reference material mounting unit 24 to cross in perpendicular to an extending line of the near infrared measuring unit 10. A reflective spectrum of the reference material 21 is used as a reference of reflective absorbance of a spectrum. The reference spectrum measurement opening and closing unit 22 is included in one side of an upper end of the reference material mounting unit 24 and is disposed between a lower side of the near infrared sensing probe 14 and an upper side of the transfer belt 51. The reference spectrum measurement opening and closing unit 22 operates according to reference spectrum measurement opening and closing signals. If the reference spectrum measurement opening and closing unit 22 receives the reference spectrum measurement opening signal, and the reference material 21 is injected into the reference spectrum measuring unit 20, the near infrared measuring unit 10 measures a spectrum of the reference material 21. The reference spectrum measurement opening and closing unit 22 receives the reference spectrum measurement closing signal, removes the reference material 21 from the reference spectrum measuring unit 20, and is closed. The reference spectrum measuring unit 20 and the near infrared measuring unit 10 are separated from the red pepper powder transferring unit 50 in order to prevent the reference spectrum measuring unit 20 and the near infrared measuring unit 10 from being contaminated by the red pepper powder or impurities and precisely measure a reference spectrum. A floor surface of the reference spectrum measuring unit 20 is formed of a material such as crystal having excellent near infrared transmittance characteristics. The reference material 21 is injected into and removed from the reference spectrum measuring unit 20 through a front and back linear motion or a left and right rotation motion. When a measurement controller is used, the measurement controller may receive the reference spectrum measurement opening and closing signals and control the reference spectrum measurement opening and closing unit 22.

The red pepper powder injecting unit 30 is included in one side of the transfer belt 51 and includes an injection tub 31, an injection opening and closing unit 32, an injection and block notice sensor 33, and an agitator 34. The injection tub 31 is in the form of a hopper, has an inlet in an upper side thereof and an outlet in a lower side thereof, and temporally contains and injects the red pepper powder used to measure pungency.

Figure 3:
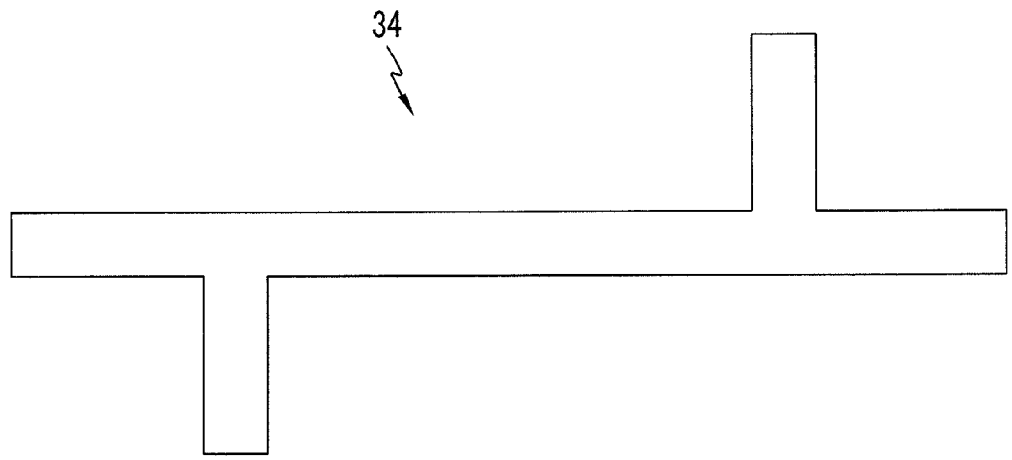
FIG. 3 illustrates an agitator of a red pepper powder injection unit according to an embodiment of the present invention.

FIG. 3 illustrates the agitator 34 of the red pepper powder injection unit 30 according to an embodiment of the present invention. Referring to FIG. 3, the agitator 34 is included in an upper side of the injection opening and closing unit 32 in a lower portion of the injection tub 31 and includes two or more agitation wings. The agitator 34 prevents red pepper powder from being piled in the injection tub 31 and being massed and enables the red pepper powder to be smoothly injected into the injection tub 31.

The injection opening and closing unit 32 is included in an outlet end of the injection tub 31, is opened and closed according to injection and block notice signals, and enables the red pepper powder to be injected to or blocked from the transfer belt 51.

When a reference spectrum is measured, the injection opening and closing unit 32 is closed. After the reference spectrum is measured, an injection signal is transferred. If the injection signal is transferred, the injection opening and closing unit 32 is opened, and the red pepper powder is injected to the transfer belt 51. If a block signal is transferred, the injection opening and closing unit 32 is closed and blocks the red pepper powder from being injected to the transfer belt 51.

Figure 4:
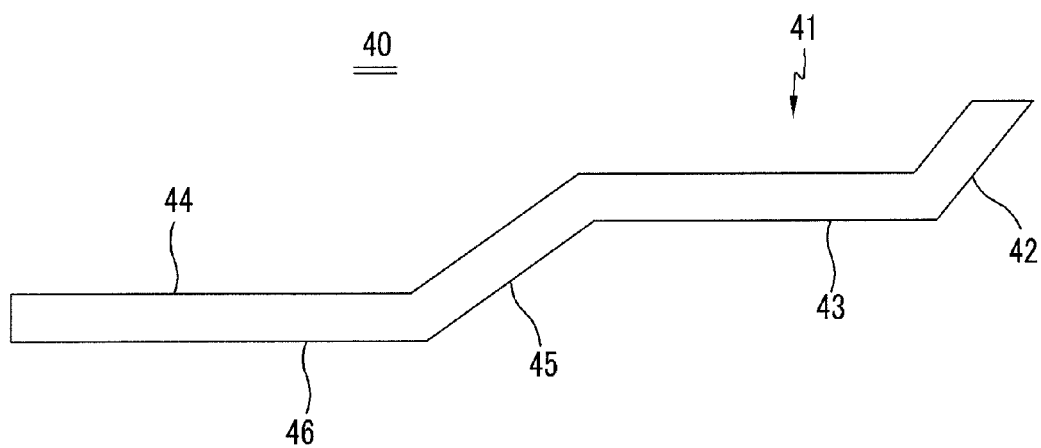
FIG. 4 illustrates a red pepper powder height equalizing unit according to an embodiment of the present invention.

FIG. 4 illustrates the red pepper powder height equalizing unit 40 according to an embodiment of the present invention.

Referring to FIG. 4, the red pepper powder height equalizing unit 40, which is a device for equalizing heights of red pepper powder injected into the near infrared measuring unit 10, includes a first height adjusting unit 41, a second height adjusting unit 44, and red pepper powder transfer guide walls 52 of the transfer belt 51, and is disposed between an outlet side of the injection tub 31 and the near infrared measuring unit 10.

The first height adjusting unit 41 includes a red pepper powder injection blocking unit 42 and a height stabilizing unit 43, adjusts transfer heights of the red pepper powder below a predetermined height, and equalizes the heights of the surface of the red pepper powder through the height stabilizing unit 43. The second height adjusting unit 44 includes a red pepper powder injection blocking unit 45 and a second height stabilizing unit 46, makes a height of the second injection blocking unit 45 lower than the first injection blocking unit 42, allows the first height adjusting unit 41 to process a portion in which heights are not equalized, and allows the second height stabilizing unit 46 to equalize the heights of the surface of the red pepper powder. The red pepper powder transfer guide walls 52 of the transfer belt 51 are included in an upper side of the transfer belt 51 and outer sides of both side surfaces of the first and second height adjusting units 41 and 44, and are used to maintain the constant height of the red pepper powder and transfer the red pepper powder. The red pepper powder height equalizing unit 40 equalizes the heights of the red pepper powder, prevents a near infrared spectrum from being irregularly reflected, and increases an accuracy of measurement.

Figure 5:
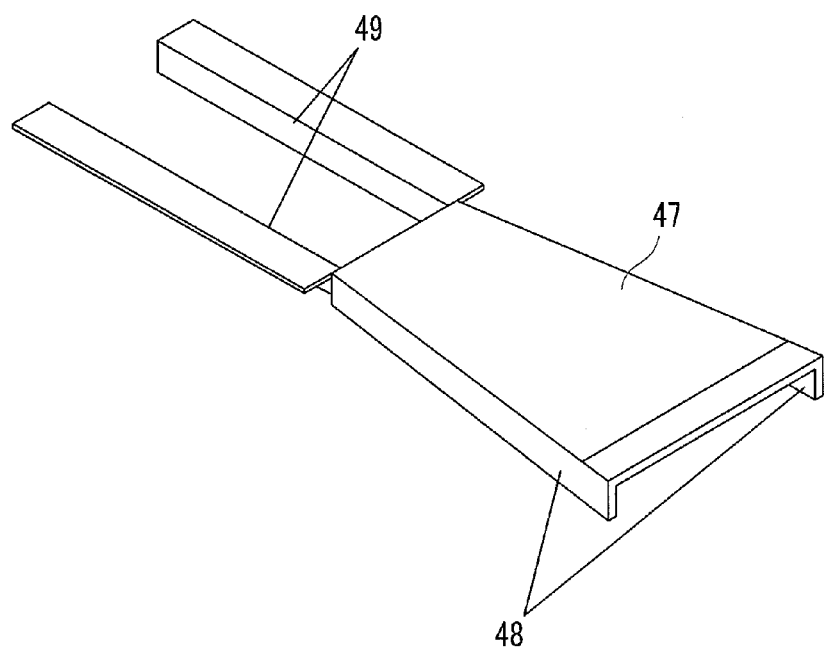
FIG. 5 illustrates a red pepper powder height equalizing unit according to another embodiment of the present invention.

FIG. 5 illustrates the red pepper powder height equalizing unit 40 according to another embodiment of the present invention.

Referring to FIG. 5, the red pepper powder height equalizing unit 40 includes the first height adjusting unit 41 and the red pepper powder transfer guide walls 52, and is disposed between the red pepper powder injecting unit 30 and the near infrared measuring unit 10.

The first height adjusting unit 41 includes a side surface compressor and an upper portion compressor, transfers red pepper powder, compresses the red pepper powder up and down and left and right simultaneously, equalizes a compression degree of the red pepper powder, and equalizes transfer heights of the red pepper powder.

The red pepper powder transfer guide walls 52 are included in one side of the first height adjusting unit 41 of an upper portion of the transfer belt 51 and include the near infrared measuring unit 10. The red pepper powder transfer guide walls 52 maintain a constant transfer height of the red pepper powder that have passed through the first height adjusting unit 41. The red pepper powder height equalizing unit 40 equalizes heights of the red pepper powder, thereby preventing a near infrared spectrum from being irregularly reflected and increasing the accuracy of measurement.

Referring to FIGS. 1 and 2, the red pepper powder transferring unit 50 includes the transfer belt 51, transfer belt driving gears 55, and a transfer motor 54, receives the red pepper powder to be measured from the red pepper powder injecting unit 30, and transfers the red pepper powder to the red pepper powder ejecting unit 60 through the near infrared measuring unit 10.

According to an embodiment of the present invention, a flat belt that does not include the red pepper powder transfer guide walls 52 in the transfer belt 51 is connected between the transfer belt driving gears 55 and operates.

According to another embodiment of the present invention, a belt that includes the red pepper powder transfer guide walls 52 in the transfer belt 51 is connected between the transfer belt driving gears 55 and operates.

Figure 6:
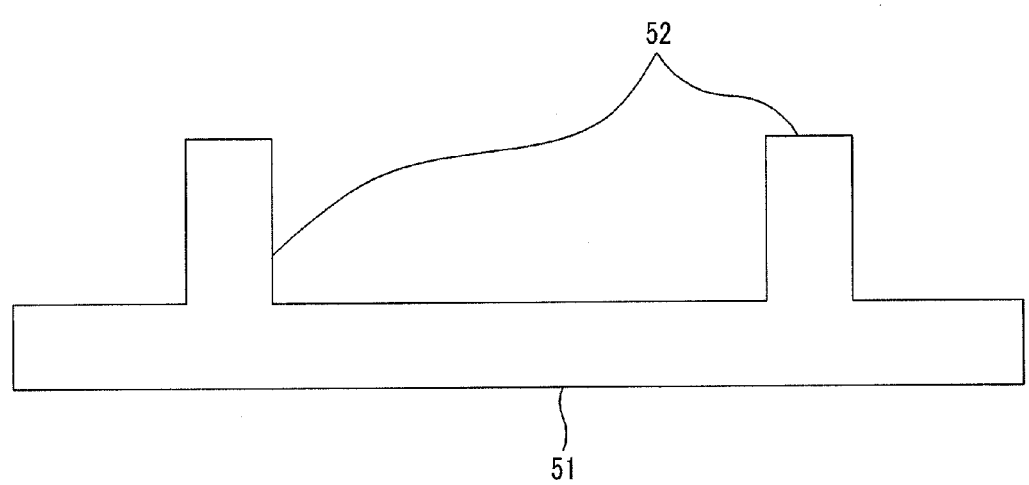
FIG. 6 illustrates red pepper powder transfer guide walls according to another embodiment of the present invention.

FIG. 6 illustrates the red pepper powder transfer guide walls 52 according to another embodiment of the present invention. The red pepper powder transfer guide walls 52 are included in an outer side of the transfer belt 51, maintain an equalized height state of red pepper powder and transfer the red pepper powder. The transfer belt driving gears 55 are included in both end portions of the transfer belt 51 and move the transfer belt 51. The transfer motor 54 is included in one side of the transfer belt driving gears 55 and drives the transfer belt driving gears 55.

Referring to FIGS. 1 and 2, the red pepper powder ejecting unit 60 drops the red pepper powder having measured pungency to an ejection tub positioned in one end of the transfer belt 51 that transfers the red pepper powder, and recollects the completely measured red pepper powder.

The PC 70 controls the driving signal of the apparatus for measuring pungency of the red pepper powder and measures pungency of the red pepper powder using the program for measuring pungency. A control program controls the reference spectrum measurement opening and closing unit 22 and the injection opening and closing unit 32. Pungency measurement software measures pungency of the red pepper powder using a capsaicinoids content measurement recurrence modeling method that uses a result of measuring capsaicinoids content that is a pungency component of the red pepper powder using a high performance liquid chromatography (HPLC) and near infrared spectrum data of the red pepper powder. The program corrects the near infrared spectrum of the measured red pepper powder to a reference spectrum and measures pungency of the red pepper powder using a pungency measurement recurrence model.

Figure 7:
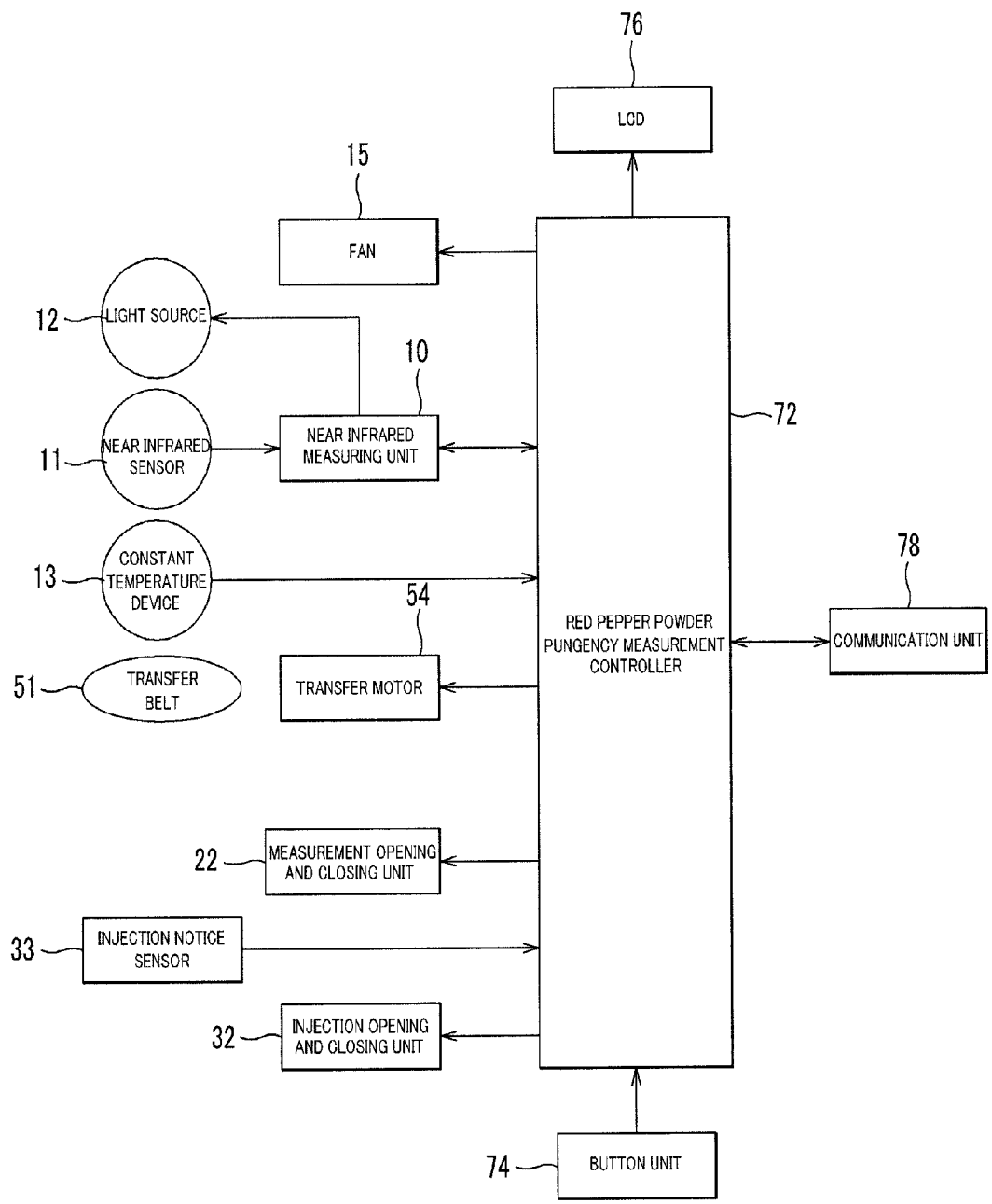
FIG. 7 is a block diagram of an apparatus for measuring pungency of red pepper powder according to a first embodiment of the present invention.

FIG. 7 is a block diagram of an apparatus for measuring pungency of red pepper powder according to a first embodiment of the present invention. A control program and a program for measuring pungency are embedded in a measurement controller board and operate without being connected to a PC.

Referring to FIG. 7, the apparatus for measuring pungency of red pepper powder of the present embodiment includes the near infrared measuring unit 10 for measuring a spectrum of the reference material 21 and measuring a spectrum of red pepper powder that is an object of measurement using the near infrared sensor 11, the light source unit 12, the near infrared sensor constant temperature device 13 for detecting a temperature of the near infrared measuring unit 10 and maintaining the constant temperature, a fan 15 for cooling the near infrared measuring unit 10 according to a control signal, a heating heater (not shown), the reference spectrum measurement opening and closing unit 22 for moving the reference material 21 according to the control of the measurement controller when reference spectrum measurement opening and closing notice signals are detected so as to measure the spectrum of the reference material 21, the injection opening and closing unit 32 for blocking the red pepper powder from injecting according to the control signal if an injection and blocking notice signal is detected, the transfer motor 54 for transferring the transfer belt 51, a button unit 74 manipulated by a measurer, an LCD 76 for displaying an operation state, a communication unit 78 for communicating an external network or a host PC, and a measurement controller 72 for operating the reference spectrum measurement opening and closing unit 22 if the reference spectrum measurement opening and closing notice signals are detected according to the manipulation of the button unit 74, moving the reference spectrum measurement opening and closing unit 22, measuring the spectrum of the reference material 21 using the near infrared measuring unit 10, if the reference spectrum measurement opening and closing notice signals are detected, closing the reference spectrum measurement opening and closing unit 22, if the red pepper powder is injected, measuring the spectrum of the red pepper powder using the near infrared measuring unit 10, receiving and correcting data of the spectrum of the reference material 21 and data of the near infrared spectrum of the red pepper powder from the near infrared measuring unit 10 and calculating and outputting a degree of pungency according to a recurrence model. The communication unit 78 may be realized as various types such as RS232C, USB, Ethernet port, etc.

The operation of the apparatus for measuring pungency of red pepper powder according to the first embodiment will now be described with reference to FIG. 8.

Figure 8:
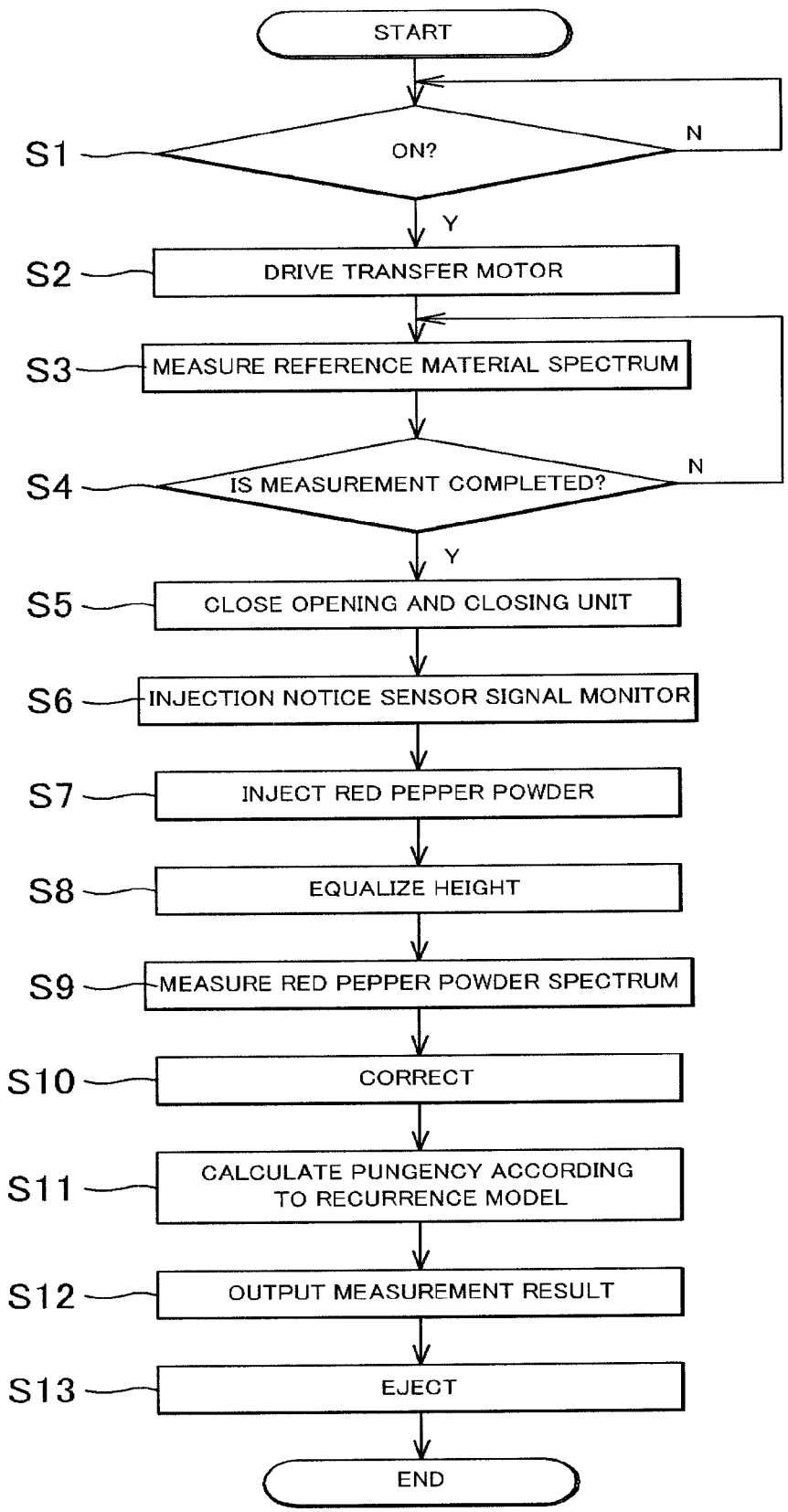
FIG. 8 is a flowchart of a method of measuring pungency of red pepper powder according to a first embodiment of the present invention.

FIG. 8 is a flowchart of a method of measuring pungency of red pepper powder according to a first embodiment of the present invention.

Referring to FIG. 8, if a red pepper powder sample to be measured by a measurer is injected into the injection tub 31 and an apparatus for measuring pungency of red pepper powder is turned on, the measurement controller 72 drives the transfer motor 54 and transfers the transfer belt 51 (S1 and S2).

The measurement controller 72 receives reference spectrum measurement opening and closing notice signals, operates the reference spectrum measurement opening and closing unit 22, moving the reference material 21, measuring a spectrum of the reference material 21 through the near infrared measuring unit 10, receiving the reference spectrum measurement opening and closing notice signals, operating the reference spectrum measurement opening and closing unit 22, and removing the reference material 21 (S3 and S4).

If a closing signal of the reference spectrum measurement opening and closing unit 22 is detected by monitoring an opening and closing state of the reference spectrum measurement opening and closing unit 22, the injection opening and closing unit 32 is opened, and the red pepper powder to be measured is injected into the transfer belt 51. If a closing signal of the injection opening and closing unit 32 is detected, the injection opening and closing unit 32 is closed in order to block the red pepper powder from being injected, and an injection of the red pepper powder is blocked (S5 through S7).

Heights of the red pepper powder injected to the transfer belt 51 are equalized by the red pepper powder height equalizing unit 40. The near infrared measuring unit 10 measures a spectrum of the red pepper powder having the equalized height using the near infrared sensor 11 (S8 and S9).

The data measured by the near infrared measuring unit 10 are input into the measurement controller 72. The measurement controller 72 corrects the near infrared spectrum of the red pepper powder to the spectrum of the reference material 21, and measures the pungency of the red pepper powder using the capsaicin content measurement recurrence modeling method (S10 and S11).

The measured pungency is output to the LCD 76 or a printer in various ways of displaying a degree of pungency.

The completely measured red pepper powder is ejected through the red pepper powder ejecting unit 60 (S12 and S13). For example, the pungency may be displayed in "very hot taste", "hot taste", "mild taste", "very mild taste", etc. for user convenience, and may be more quantitatively displayed by numerical values.

Second Embodiment

Figure 9:
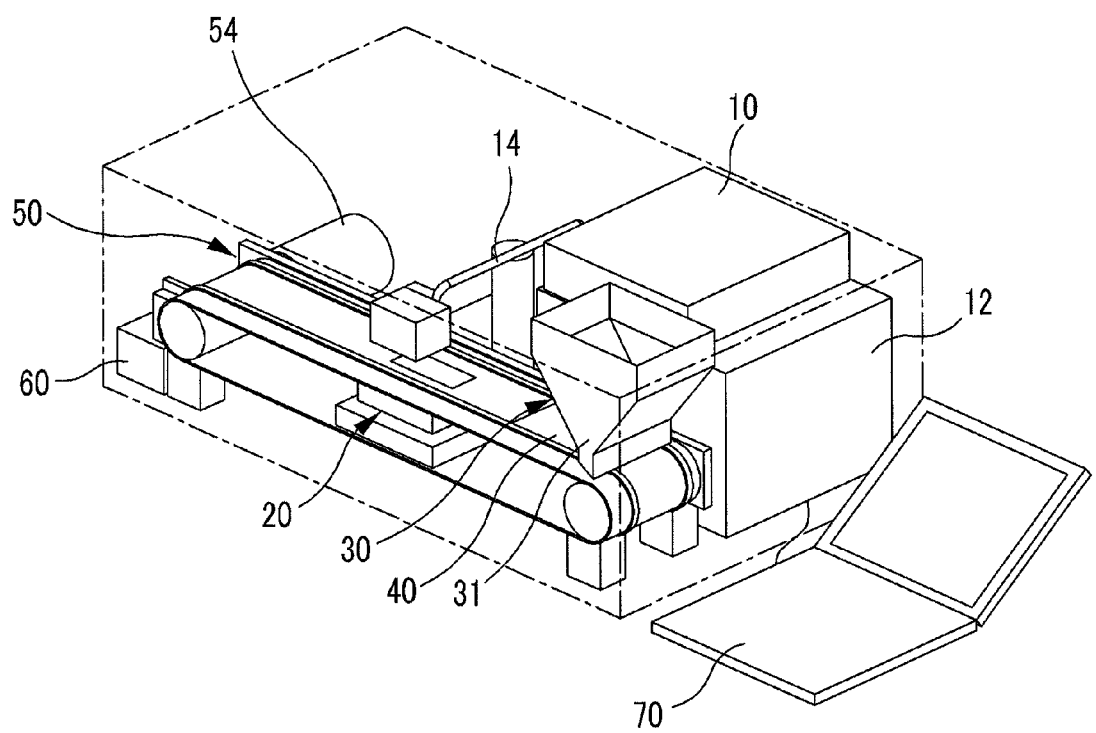
FIG. 9 is a perspective view of an apparatus for measuring pungency of red pepper powder according to a second embodiment of the present invention.
Figure 10:
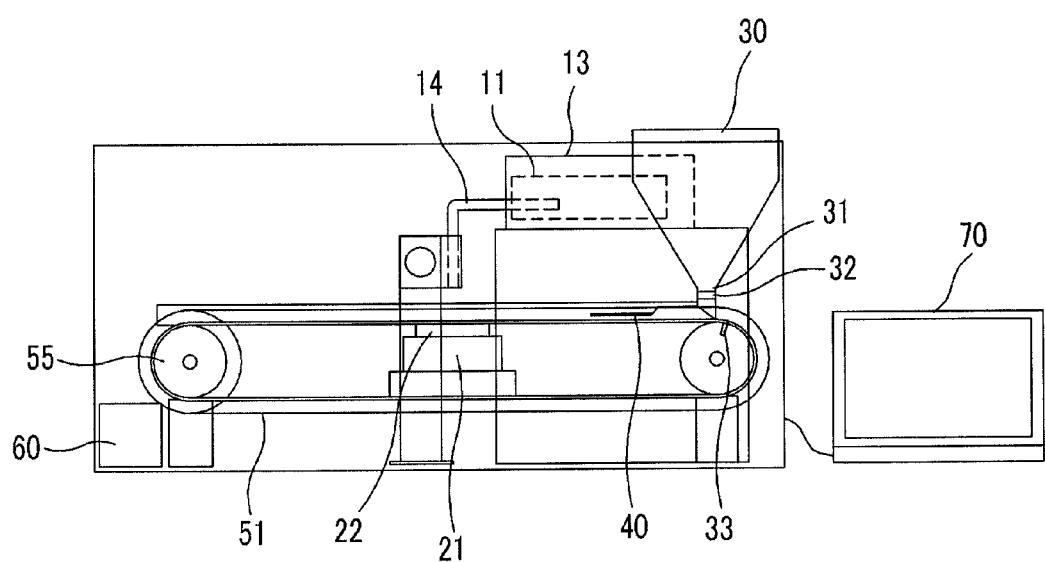
FIG. 10 is a plan view of the apparatus for measuring pungency of red pepper powder according to the second embodiment of the present invention.
Figure 11:
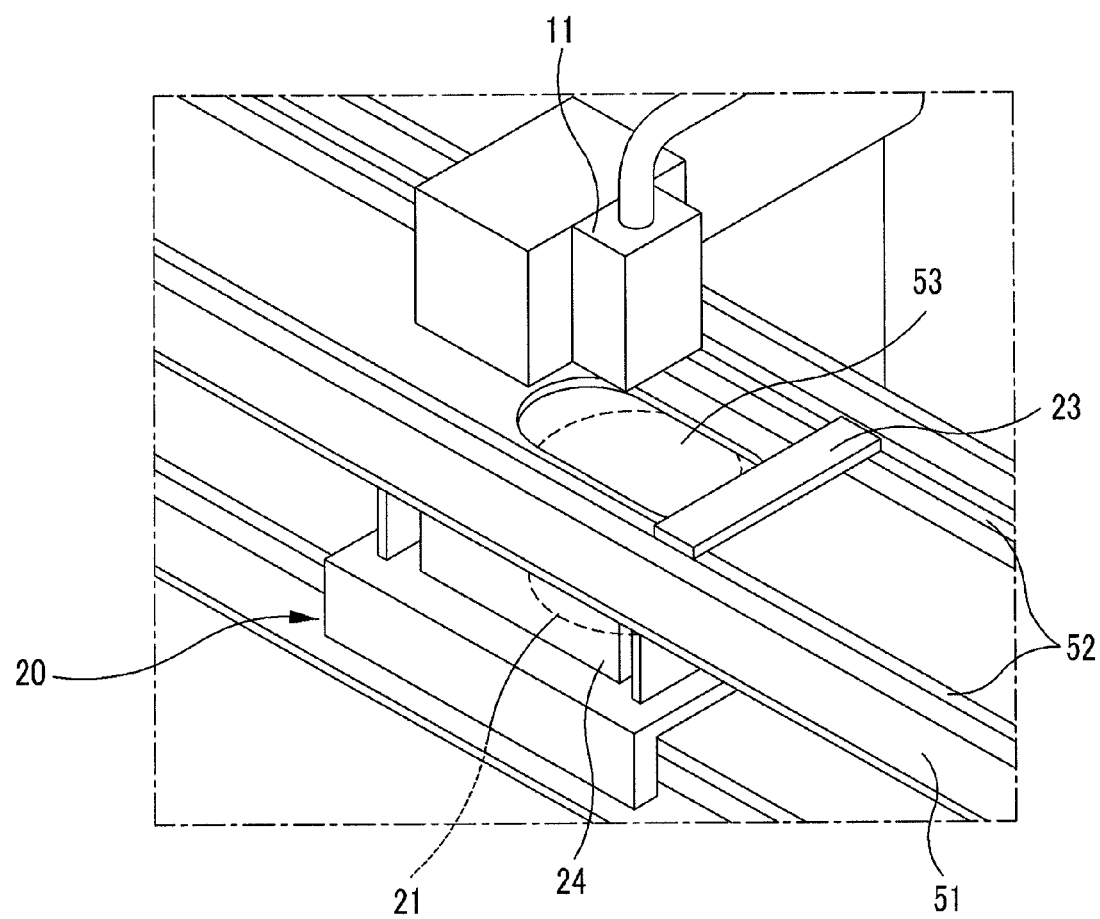
FIG. 11 illustrates a near infrared system according to the second embodiment of the present invention.

FIG. 9 is a perspective view of an apparatus for measuring pungency of red pepper powder according to a second embodiment of the present invention. FIG. 10 is a plan view of the apparatus for measuring pungency of red pepper powder according to the second embodiment of the present invention. FIG. 11 illustrates a near infrared system according to the second embodiment of the present invention.

The second embodiment is the same as the first embodiment except that a reference spectrum measuring unit is positioned in a lower side of a transfer belt and thus the difference between the first and second embodiments will now be described in order to avoid the redundancy.

FIG. 11 illustrates another example of a reference spectrum measuring unit for automatically correcting a near infrared absorbance according to the second embodiment of the present invention. When a reference spectrum measurement hole 53 of the transfer belt is positioned in a lower end of the near infrared measuring unit 10, a reference spectrum measurement opening and closing notice sensor 23 detects the reference spectrum measurement hole 53, the reference spectrum measurement opening and closing unit 22 is opened, so that the near infrared measuring unit 10 can measure a spectrum of the reference material 21.

Referring to FIG. 11, the near infrared measuring unit 10 is positioned on an upper side of red pepper powder measured by the near infrared sensor 11 including a light emitting unit and a light receiving unit. The red pepper powder is disposed on the transfer belt 51 in a lower end of the near infrared sensor 11. The reference spectrum measuring unit 20 is positioned in a lower end of the transfer belt 51. In general, an edible portion of the red pepper powder includes a pericarp, placenta, and seed. Although the placenta is a very small amount, capsaicinoids content of the placenta is several tens of times compared to that of the pericarp or the seed. Thus, although pungency of the red pepper powder is almost determined according to an amount of placenta contained in the red pepper powder, the placenta has an ununiform distribution and thus pungency differs according to sampling. In order to remove such an error of pungency by sampling, the present invention scans surface of the red pepper powder, obtains a near infrared spectrum, and measures spectrum of the whole red pepper powder. The apparatus for measuring pungency of the red pepper powder according to the present invention measures a spectrum of the reference material 21, measures the spectrum of the red pepper powder, and corrects sensitivity of the red pepper powder to the spectrum of the reference material 21 in order to reduce an error of the spectrum of the red pepper powder.

The reference spectrum measuring unit 20 includes the reference material 21, the reference spectrum measurement opening and closing unit 22, the reference spectrum measurement opening and closing notice sensor 23, the reference material mounting unit 24, the reference spectrum measurement hole 53 of the transfer belt 51. The reference material mounting unit 24 is positioned in a perpendicular lower side of the near infrared measuring unit 10, and has the surface of the reference material 21 mounted in perpendicular to the near infrared measuring unit 10. The reference material 21 is formed of Teflon and is fixed to the reference material mounting unit 24 to cross in perpendicular to an extending line of the near infrared measuring unit 10. A reflective spectrum of the reference material 21 is used as a reference of reflective absorbance of a spectrum. The reference spectrum measurement opening and closing unit 22 is included in one side of an upper end of the reference material mounting unit 24 and is disposed in a lower portion of the transfer belt 51. The reference spectrum measurement opening and closing unit 22 operates according to reference spectrum measurement opening and closing signals. If the reference spectrum measurement opening and closing unit 22 receives the reference spectrum measurement opening signal and is opened, the near infrared measuring unit 10 measures a spectrum of the reference material 21. The reference spectrum measurement opening and closing unit 22 receives the reference spectrum measurement closing signal and is closed. The reference spectrum measurement opening and closing notice sensor 23 is positioned in an upper portion of the transfer belt 51 between the near infrared measuring unit 10 and the red pepper powder height equalizing unit 40. If a start portion of the reference spectrum measurement hole 53 is detected, the reference spectrum measurement opening and closing notice sensor 23 sends a signal to open the reference spectrum measurement opening and closing unit 22. If an end portion of the reference spectrum measurement hole 53 is detected, the reference spectrum measurement opening and closing notice sensor 23 sends a signal to close the reference spectrum measurement opening and closing unit 22. The reference spectrum measurement opening and closing unit 22 and the reference spectrum measurement opening and closing notice sensor 23 prevent the reference material 21 from being contaminated by the red pepper powder or impurities and precisely measure a reference spectrum. When a measurement controller is used, the measurement controller may receive a signal of the reference spectrum measurement opening and closing notice sensor 23 and control the reference spectrum measurement opening and closing unit 22.

Referring to FIGS. 9 and 10, the injection opening and closing unit 32 is included in an outlet end of the injection tub 31, is opened and closed according to a signal of the injection and block notice sensor 33, and enables the red pepper powder to be injected to or blocked from the transfer belt 51. The injection and block notice sensor 33 is included in one side of the transfer belt driving gears 55 around the red pepper powder injection unit 30, detects the start portion of the reference spectrum measurement hole 53, closes the injection opening and closing unit 32, and prevents the red pepper powder from being injected into the reference spectrum measurement hole 53, detects the end portion of the reference spectrum measurement hole 53, opens the injection opening and closing unit 32, and enables the red pepper powder to be injected to the transfer belt 51. The red pepper powder is agitated and injected to the transfer belt 51. If an injection signal of the injection and block notice sensor 33 is transferred, the injection opening and closing unit 32 is opened and the red pepper powder is injected. If a blocking signal of the injection and block notice sensor 33 is transferred, the injection opening and closing unit 32 is closed and an injection of the red pepper powder is blocked.

The red pepper powder injecting unit 30, the agitator 34, the red pepper powder height equalizing unit 40, and the red pepper powder transferring unit 50 are the same as described in the first embodiment and thus the detailed descriptions thereof are not repeated here.

Figure 12:
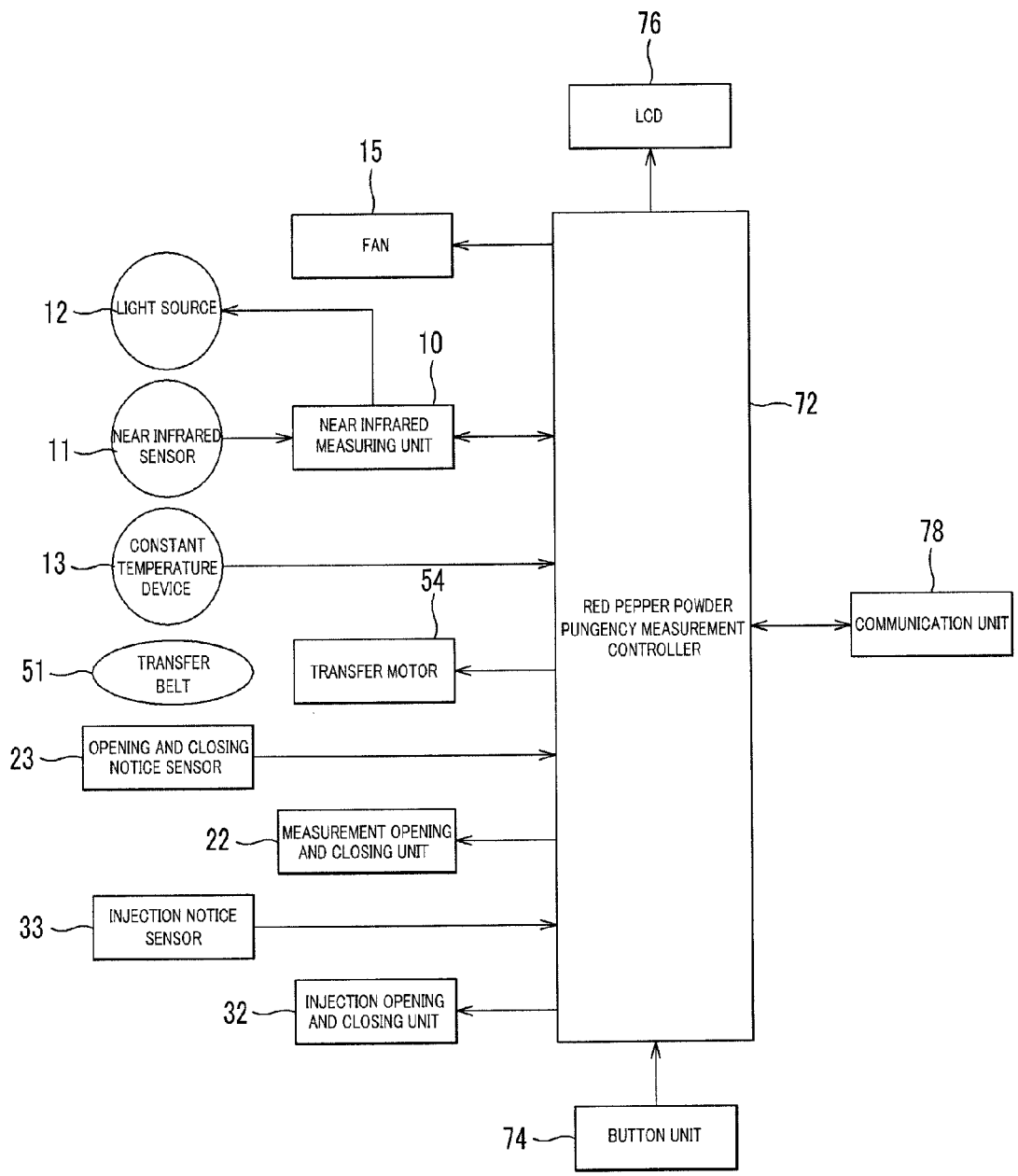
FIG. 12 is a block diagram of an apparatus for measuring pungency of red pepper powder according to the second embodiment of the present invention.

FIG. 12 is a block diagram of an apparatus for measuring pungency of red pepper powder according to the second embodiment of the present invention.

A control program and a program for measuring pungency are embedded in a measurement controller board and operate without being connected to a PC.

Referring to FIG. 12, the apparatus for measuring pungency of red pepper powder of the present embodiment includes the near infrared measuring unit 10 for measuring a spectrum of the reference material 21 and measuring a spectrum of red pepper powder that is an object of measurement using the near infrared sensor 11, the light source unit 12, the near infrared sensor constant temperature device 13 for maintaining a constant temperature of the near infrared measuring unit 10, the fan 15 for cooling the near infrared measuring unit 10 according to a control signal, the reference spectrum measurement opening and closing notice sensor 23 for detecting the reference spectrum measurement hole 53 of the transfer belt 51 in order to measure the spectrum of the reference material 21, the reference spectrum measurement opening and closing unit 22 that is opened and closed to measure the spectrum of the reference material 21 according to the control of the measurement controller 72 if the reference spectrum measurement opening and closing notice sensor 23 detects the reference spectrum measurement hole 53, the injection opening and closing unit 32 for blocking the injection and block notice sensor 33 for detecting the reference spectrum measurement hole 53 for preventing the red pepper powder from being injected into the reference spectrum measurement hole 53 of the transfer belt 51 and blocking the red pepper powder from being injected according to the control signal if the injection and block notice sensor 33 detects the reference spectrum measurement hole 53, the transfer motor 54 for transferring the transfer belt 51, the button unit 74 manipulated by a measurer, the LCD 76 for displaying an operation state, the communication unit 78 for communicating an external network or a host PC, and the measurement controller 72 for opening the reference spectrum measurement opening and closing unit 22 if a start point of the reference spectrum measurement hole 53 of the transfer belt 51 is detected according to the manipulation of the button unit 74, measuring the spectrum of the reference material 21 using the near infrared measuring unit 10 through the reference spectrum measurement hole 53 of the transfer belt 51, if the reference spectrum measurement hole 53 of the transfer belt 51 is passed through, closing the reference spectrum measurement opening and closing unit 22, if the red pepper powder is injected, measuring the spectrum of the red pepper powder using the near infrared measuring unit 10, receiving and correcting data of the spectrum of the reference material 21 and data of the near infrared spectrum of the red pepper powder from the near infrared measuring unit 10 and calculating and outputting a degree of pungency according to a recurrence model. The communication unit 78 may be realized as various types such as RS232C, USB, Ethernet port, etc.

Thereafter, the operation of the apparatus for measuring pungency of red pepper powder according to the second embodiment will now be described with reference to FIG. 13.

Figure 13:
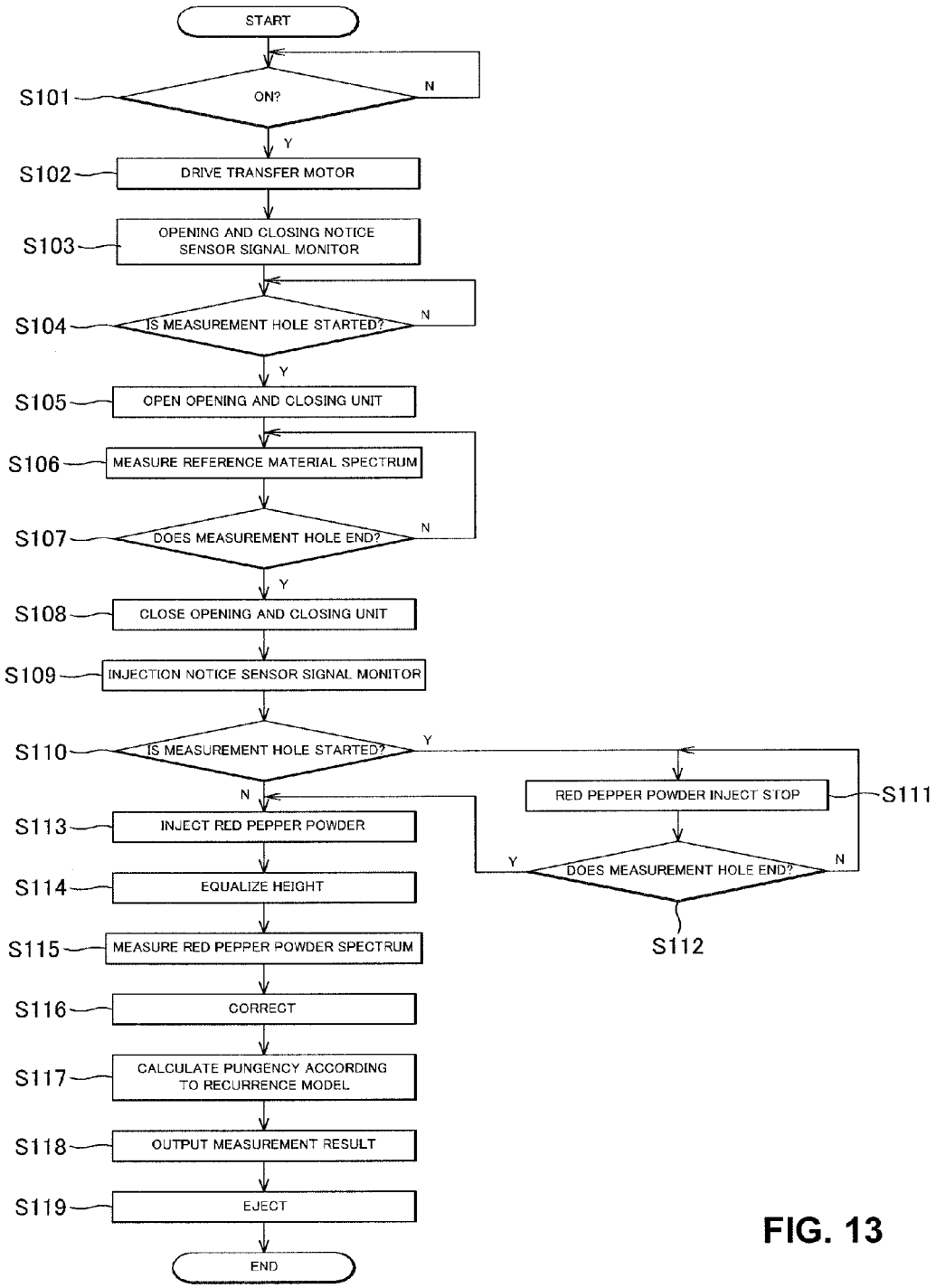
FIG. 13 is a flowchart of a method of measuring pungency of red pepper powder according to a second embodiment of the present invention.

FIG. 13 is a flowchart of a method of measuring pungency of red pepper powder according to a second embodiment of the present invention.

Referring to FIG. 13, if a red pepper powder sample to be measured by a measurer is injected into the injection tub 31 and an apparatus for measuring pungency of red pepper powder is turned on, the measurement controller 72 drives the transfer motor 54 and transfers the transfer belt 51 in which the reference spectrum measurement hole 53 is formed (S101 and S102).

The measurement controller 72 monitors a signal of the reference spectrum measurement opening and closing notice sensor 23, if a start point of the reference spectrum measurement hole 53 is detected, opens the reference spectrum measurement opening and closing unit 22, and measures the spectrum of the reference material 21 through the near infrared measuring unit 10 (S103 through S106).

If an end point of the reference spectrum measurement hole 53 is detected, the measurement controller 72 closes the reference spectrum measurement opening and closing unit 22, monitors a signal of the injection and block notice sensor 33, if the reference spectrum measurement hole 53 is not detected, opens the injection opening and closing unit 32, and injects the red pepper powder to be measured to the transfer belt 51. If the reference spectrum measurement hole 53 is detected, the measurement controller 72 closes the injection opening and closing unit 32 so as to prevent the red pepper powder from being injected into the reference spectrum measurement hole 53, and blocks an injection of the red pepper powder (S107 through S113).

Heights of the red pepper powder injected to the transfer belt 51 are equalized by the red pepper powder height equalizing unit 40. The near infrared measuring unit 10 measures a spectrum of the red pepper powder having the equalized height using the near infrared sensor 11 (S114 and S115).

The data measured by the near infrared measuring unit 10 are input into the measurement controller 72. The measurement controller 72 corrects the near infrared spectrum of the red pepper powder to the spectrum of the reference material 21, and measures the pungency of the red pepper powder using the capsaicinoids content measurement recurrence modeling method (S116 and S117).

The measured pungency is output to the LCD 76 or a printer in various ways of displaying a degree of pungency. The completely measured red pepper powder is ejected through the red pepper powder ejecting unit 60 (S118 and S119). For example, the pungency may be displayed in "very pungency", "pungency", "mild taste", "very mild taste", etc. for user convenience, and may be more quantitatively displayed by numerical values.

The apparatus for measuring pungency of red pepper powder according to the present invention objectively measures and displays the degree of pungency of red pepper powder based on near infrared spectrum data, which makes it possible to standardize the degree of pungency of red pepper powder, so that consumers can select a degree of pungency of red pepper powder according to their respective preferences, which improves quality of a dietary life.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for measuring pungency of red pepper powder comprising:
    a near infrared measuring unit for measuring a spectrum of a reference material or a near infrared spectrum of red pepper powder that is an object of measurement according to a control signal using a near infrared sensor;
    a reference spectrum measuring unit for enabling the near infrared measuring unit to measure the spectrum of the reference material;

a red pepper powder injecting unit for injecting a sample of the red pepper powder that is the object of measurement;

a red pepper powder height equalizing unit for equalizing heights of the red pepper powder injected through the red pepper powder injecting unit in order to increase the accuracy of measurement;

a red pepper powder transferring unit for transferring the red pepper powder that is the object of measurement via a transfer belt;

a red pepper powder ejecting unit for ejecting the completely measured sample of the red pepper powder;

a display unit for displaying an operation state or a degree of pungency of measurement result;

a button unit; and a measurement controller for, if a reference spectrum measurement opening signal is detected, operating a reference spectrum measurement opening and closing unit, injecting the reference material, measuring the spectrum of the reference material using the near infrared measuring unit, if the reference spectrum measurement closing signal is detected, operating the reference spectrum measurement opening and closing unit, removing the reference material, closing the reference spectrum measurement opening and closing unit, injecting the red pepper powder, and measuring the near infrared spectrum of red pepper powder using the near infrared measuring unit, correcting near infrared spectrum data of the red pepper powder input from the near infrared measuring unit to the spectrum of the reference material, calculating a degree of pungency according to a capsaicinoids content measurement recurrence model, and displaying the degree of pungency on the display unit.

2. The apparatus of claim 1, wherein the near infrared measuring unit is positioned on an upper side of the reference spectrum measuring unit, wherein the reference spectrum measuring unit is positioned on an upper side of the transfer belt, and comprises the reference material, a reference material mounting unit for accommodating the reference material, and a reference spectrum measurement opening and closing unit for, if a reference spectrum measurement opening and closing notice signal is transferred, operating to move the reference material toward the near infrared measuring unit, and, if the reference spectrum measurement is completed, being closed to remove the reference material from the near infrared measuring unit.

3. The apparatus of claim 1, wherein the red pepper powder injecting unit comprises:

an injection tub positioned in one side of the transfer belt, and for temporally containing and injecting the red pepper powder to be measured;

an agitator for agitating the red pepper powder injected into the injection tub to prevent the red pepper powder from being piled in the injection tub and massed; and an injection opening and closing unit for, if an injection notice signal is detected, opening an outlet of the injection tub and injecting the red pepper powder to the transfer belt, and, if a blocking notice signal is detected, closing the outlet of the injection tub.

4. The apparatus of claim 1, wherein the red pepper powder height equalizing unit comprises:

a first height adjusting unit comprising a first red pepper powder injection blocking unit and a first height stabilizing unit, for adjusting transfer heights of the red pepper powder below a predetermined height, and equalizing the heights of the surface of the red pepper powder through the first height stabilizing unit;

a second height adjusting unit comprising a second red pepper powder injection blocking unit and a second height stabilizing unit, for making a height of the second injection blocking unit lower than the first injection blocking unit, allowing the first height adjusting unit to process a portion in which heights are not equalized and equalize the heights of the surface of the red pepper powder, wherein equalizing of the heights of the red pepper powder prevents a near infrared spectrum from being irregularly reflected.

5. The apparatus of claim 1, wherein the red pepper powder height equalizing unit comprises: a first height adjusting unit and red pepper powder transfer guide walls, and is disposed between an outlet side of the injection tub and the near infrared measuring unit, wherein the height adjusting unit comprises a side surface compressor and an upper portion compressor, and the red pepper powder transfer guide walls are disposed in one side of the first height adjusting unit of the upper side portion of the transfer belt, wherein the compression degree of the red pepper powder is equalized and heights thereof are equalized so that the near infrared spectrum is prevented from irregularly reflecting.

6. The apparatus of claim 1, wherein the measurement controller measures pungency of the red pepper powder using a capsaicinoids content measurement recurrence modeling method that uses a result of measuring capsaicinoids content that is a pungency component of the red pepper powder using a high performance liquid chromatography (HPLC) and near infrared spectrum data of the red pepper powder.

7. The apparatus of claim 1, further comprising: a communication unit for communicating an external network or a host PC.

8. An apparatus for measuring pungency of red pepper powder comprising:

a near infrared measuring unit for measuring a spectrum of a reference material or a near infrared spectrum of red pepper powder that is an object of measurement according to a control signal using a near infrared sensor;

a reference spectrum measuring unit for enabling the near infrared measuring unit to measure the spectrum of the reference material;

a red pepper powder injecting unit for injecting a sample of the red pepper powder that is the object of measurement;

a red pepper powder height equalizing unit for equalizing heights of the red pepper powder injected through the red pepper powder injecting unit in order to increase the accuracy of measurement;

a red pepper powder transferring unit for transferring the red pepper powder that is the object of measurement via a transfer belt in which a measurement hole is formed in order to measure the spectrum of the reference material;

a red pepper powder ejecting unit for ejecting the completely measured sample of the red pepper powder;

a display unit for displaying an operation state or a degree of pungency of measurement result;

a button unit; and a measurement controller for controlling a general operation according to manipulation of the button unit, if a start of the measurement hole of the transfer belt is detected, opening a reference spectrum measurement opening and closing unit of the reference spectrum measuring unit, measuring the spectrum of the reference material using the near infrared measuring unit through the measurement hole of the transfer belt, if the measurement hole is passed through, closing the reference spectrum measurement opening and closing unit, injecting the red pepper powder, measuring the spectrum of the red pepper powder using the near infrared measuring unit, correcting data of the near infrared spectrum of the red pepper powder input from the near infrared measuring unit to the spectrum of the reference material, calculating a degree of pungency according to a capsaicinoids content measurement recurrence model, and displaying the degree of pungency on the display unit.

9. The apparatus of claim 8, wherein the near infrared measuring unit is positioned on an upper side of the transfer belt,
wherein the reference spectrum measuring unit is positioned on a lower side of the transfer belt, and comprises the reference material, a reference material mounting unit for accommodating the reference material, a reference spectrum measurement opening and closing notice sensor for detecting the measurement hole of the transfer belt, and a reference spectrum measurement opening and closing unit for being opened to expose the reference material toward the near infrared measurement unit, if the reference spectrum measurement opening and closing notice sensor detects the measurement hole, and being closed, if the measurement hole is passed through.

10. The apparatus of claim 8, wherein the red pepper powder injecting unit comprises:
an injection tub positioned in one side of the transfer belt, and for temporally containing and injecting the red pepper powder to be measured;
an agitator for agitating the red pepper powder injected into the injection tub to prevent the red pepper powder piled in the injection tub from being massed;
an injection and blocking notice sensor for detecting the measurement hole; and
an injection opening and closing unit for, if the measurement hole is not detected, opening an outlet of the injection tub and injecting the red pepper powder to the transfer belt, and, if the measurement hole is detected, closing the outlet of the injection tub and preventing the measurement hole from being contaminated by the red pepper powder.

11. The apparatus of claim 8, wherein the red pepper powder transfer unit comprises:
a transfer belt in which the measurement hole is formed in one side of a central portion and red pepper powder transfer guide walls for maintaining constant heights of the red pepper powder in both sides thereof, transfer belt driving gears for driving the transfer belt, and a transfer motor for transferring the transfer belt through the transfer belt driving gears according to the control of the measurement controller.

12. The apparatus of claim 8, wherein the red pepper powder height equalizing unit comprises:
a first height adjusting unit comprising a first red pepper powder injection blocking unit and a first height stabilizing unit, for adjusting transfer heights of the red pepper powder below a predetermined height, and equalizing the heights of the surface of the red pepper powder through the first height stabilizing unit;
a second height adjusting unit comprising a second red pepper powder injection blocking unit and a second height stabilizing unit, for making a height of the second injection blocking unit lower than the first injection blocking unit, allowing the first height adjusting unit to process a portion in which heights are not equalized and equalize the heights of the surface of the red pepper powder,
wherein equalizing of the heights of the red pepper powder prevents a near infrared spectrum from being irregularly reflected.

13. The apparatus of claim 8, wherein the red pepper powder height equalizing unit comprises: a first height adjusting unit and red pepper powder transfer guide walls, and is disposed between an outlet side of the injection tub and the near infrared measuring unit,
wherein the height adjusting unit comprises a side surface compressor and an upper portion compressor, and the red pepper powder transfer guide walls are disposed in one side of the first height adjusting unit of the upper side portion of the transfer belt,
wherein the compression degree of the red pepper powder is equalized and heights thereof are equalized so that the near infrared spectrum is prevented from irregularly reflecting.

14. The apparatus of claim 8, wherein the measurement controller measures pungency of the red pepper powder using a capsaicinoids content measurement recurrence modeling method that uses a result of measuring capsaicinoids content that is a pungency component of the red pepper powder using a high performance liquid chromatography (HPLC) and near infrared spectrum data of the red pepper powder.

15. The apparatus of claim 8, further comprising: a communication unit for communicating an external network or a host PC.

* * * * *